United States Patent [19]

Klingenbeck et al.

[11] Patent Number: 4,914,681
[45] Date of Patent: Apr. 3, 1990

[54] COMPUTER TOMOGRAPHY APPARATUS

[75] Inventors: Klaus Klingenbeck, Hessdorf; Arnulf Oppelt, Spardorf, both of Fed. Rep. of Germany

[73] Assignee: Siemens Aktiengesellschaft, Berlin and Munich, Fed. Rep. of Germany

[21] Appl. No.: 121,060

[22] Filed: Nov. 16, 1987

[30] Foreign Application Priority Data

Nov. 25, 1986 [DE] Fed. Rep. of Germany ....... 3640195

[51] Int. Cl.$^4$ ............................................. H01J 35/30
[52] U.S. Cl. ........................................ 378/12; 378/10; 378/137
[58] Field of Search ............... 378/10, 12, 17, 137, 378/138

[56] References Cited

U.S. PATENT DOCUMENTS

| | | |
|---|---|---|
| 4,130,759 | 12/1978 | Haimson . |
| 4,135,095 | 1/1979 | Watanabe ............................. 378/10 |
| 4,158,142 | 6/1979 | Haimson . |
| 4,206,356 | 6/1980 | Wardley et al. ..................... 378/17 |
| 4,352,021 | 9/1982 | Boyd et al. . |
| 4,392,235 | 7/1983 | Houston .............................. 378/10 |
| 4,631,741 | 12/1986 | Rand et al. ......................... 378/10 |
| 4,748,650 | 5/1988 | Ammann ............................. 378/137 |

Primary Examiner—Carolyn E. Fields
Assistant Examiner—David P. Porta
Attorney, Agent, or Firm—Hill, Van Santen, Steadman & Simpson

[57] ABSTRACT

A computer tomography apparatus has an annular anode surrounding a volume in which an examination subject is disposed, a source for generating an electron beam, and a coil through which the electron beam passes which deflects the electron beam so as to be incident on a face of the anode and to orbit the examination subject, thereby causing the examination subject to be irradiated in a measuring field from various directions. A control unit is provided for the coil causing the electron beam to be deflected so as to sweep the anode in both the azimuthal and radial directions. The focus of the electron beam on the anode surface thus describes a wave-shaped path, so that the focus path on the anode is lengthened and the thermal load is reduced.

8 Claims, 2 Drawing Sheets

COMPUTER TOMOGRAPHY APPARATUS

BACKGROUND OF THE INVENTION

1. Field of the Invention

The present invention is directed to a computer tomography apparatus, and in particular to such an apparatus having an annular anode surrounding a measuring field in which a patient is disposed, and means for causing an electron beam to orbit the patient while incident on the anode, so that x-radiation is generated in the measuring field from different directions.

2. Description of the Prior Art

Various types of computer tomography devices are known wherein a measuring installation consisting of an x-ray source and a radiation detector is mechanically moved around a measuring field in which the patient is disposed. Computer tomography devices of this type thus require the relatively heavy components to be mechanically moved for scanning the entire measuring field. Another type of computer tomography apparatus employs a ring-shaped anode which surrounds the measuring field, and a coil is provided through which the electron beam passes so as to deflect the electron beam onto a surface of the anode in an orbit around the patient. Trans-irradiation of the patient disposed in the measuring field from a number of different directions can thus be undertaken very quickly, so that a cross-sectional image of the slice of the patient disposed in the measuring field can be generated in an extremely short time.

The electron beam required for generating the x-radiation is emitted by an electron gun, and is electron-optically focused onto the anode surface by means of electrical and/or magnetic lenses. The required orbital movement of the electron beam is achieved using an electrical or magnetic deflecting field which is continually changed in orientation to deflect the electron beam as desired.

A focus of the electron beam on the anode surface which is as close to a point as possible is required for achieving a high image sharpness in the resulting x-ray image. A true point focus, however, would lead to local over heating at the anode surface, and would result in the destruction thereof. The focal spot must therefore be "stretched." The enlarged focal spot is ideally a rectangle having, for example, a side ratio of 6:1. If the surface of the anode on which the electron beam is incident is disposed at a small angle of, for example, 10° relative to the emission direction of the x-radiation, the projection of the focus on this surface will have the required punctiform shape. The actual electron focal spot on the anode surface will thus be relatively large, and result in a correspondingly reduced thermal load on the anode, but will have optical properties corresponding to a relatively small focal spot.

In conventional orbiting type computer tomography devices, expanding the focal spot along its longitudinal direction requires relatively complex electron-optical auxiliary means.

A computer tomography apparatus is disclosed in German No. OS 28 11 464, corresponding to U.S. Pat. Nos. 4,130,759 and 4,158,142 wherein deflection of the electron beam in the radial direction on the annular anode is undertaken so that the electron beam is alternatingly incident on the anode and on a separate beam collector. The beam collector does not function to generate x-radiation. The path of the electron beam on the anode surface, accordingly, is not continuous, but is an interrupted path.

SUMMARY OF THE INVENTION

It is an object of the present invention to provide an orbiting electron beam computer tomography apparatus which has a punctiform optical focal spot, but avoids thermal overloading of the anode without expanding the focal spot in its longitudinal direction.

The above object is achieved in accordance with the principles of the present invention in a computer tomography apparatus having a control unit for the coil which deflects the electron beam which causes the electron beam to scan or sweep the surface of the anode both in the azimuthal direction and the radial direction, so that the focus on the anode describes an uninterrupted wave-shaped path. The normal deflecting field is superimposed by the operation of the control unit with a periodically varying auxiliary field, so that the electron beam oscillates on the anode transversely relative to the circumferential direction of the anode. The path of the focus on the anode surface is thus enlarged and local heating is reduced.

The preiodically varying auxiliary field can be simply generated by periodically varying the currents or voltages required for deflecting the electron beam which are supplied to the coil. Periodic deflection of the focus around a circle on the anode surface which is concentric with the anode, however, results in artifacts in the x-ray image if the sweep frequency is not substantially greater than the sampling frequency which is employed for making the projections. The orbital, sampling and sweep frequencies must therefore be synchronized. It is preferable to undertake such synchronization such that one-fourth or one-half of a period of the sweep frequency, or a whole multiple thereof, is within the time between the registration of two samples belonging to a projection. A further improvement is achieved if the synchronization is undertaken such that the focus of the electron beam crosses the center circle on the anode at the respective sampling times, or if the maxima or minima of the radial deflection coincide with the sampling points in time.

In accordance with the principles of the present invention, not only are x-ray image artifacts reduced, but also the sweep frequency is reduced to one-half or one-fourth of the sampling frequency for an individual projection. This permits higher inductances at the coils of the deflection field, so that lower deflection currents are possible, with correspondingly lower demands on the power gain of the deflection and sweep generator.

DESCRIPTION OF THE PREFERRED EMBODIMENTS

Figure 1:
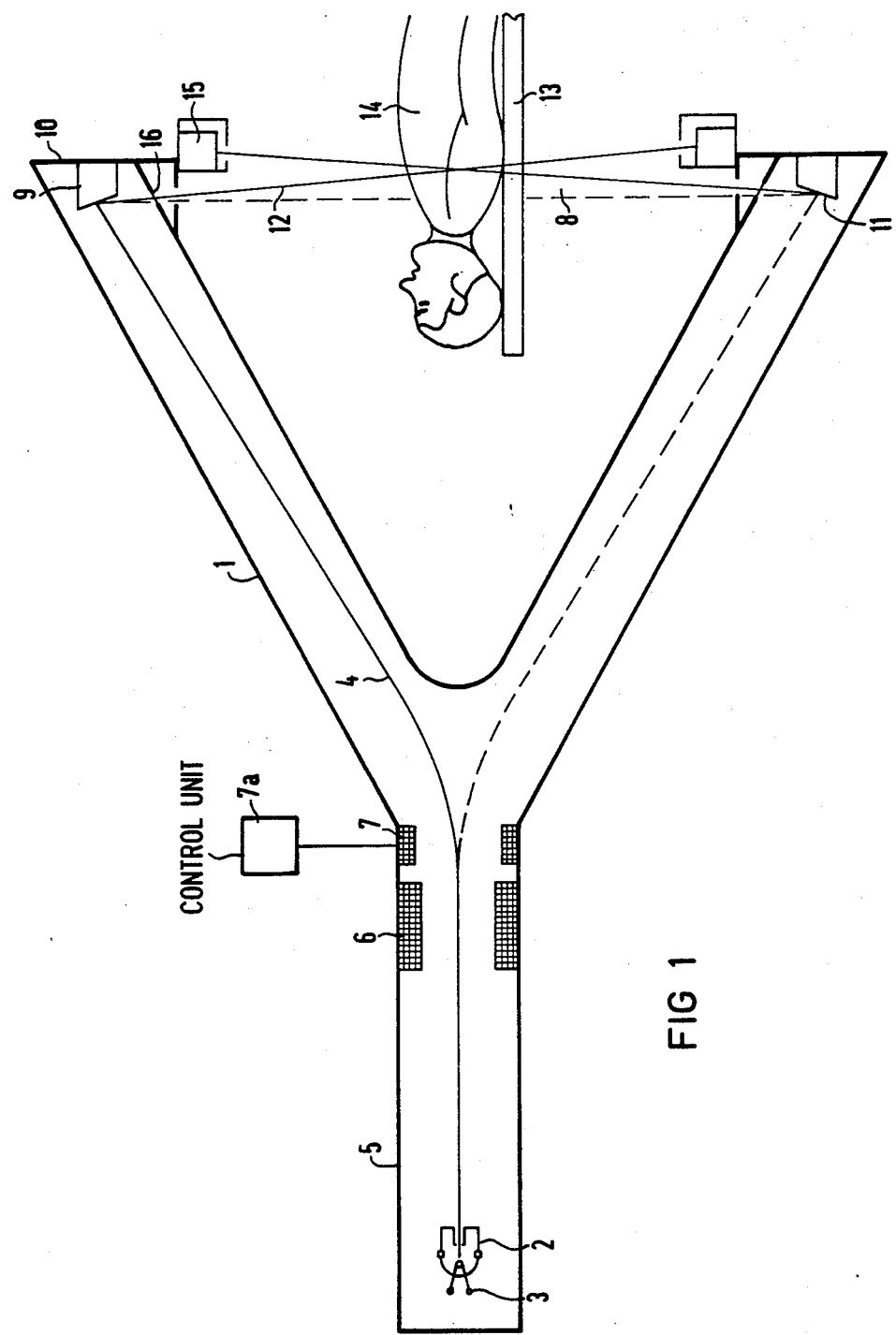
FIG. 1 is a side sectional view of the components of a computer tomography apparatus constructed in accordance with the principles of the present invention necessary to explain the operation thereof.

As shown in FIG. 1, the computer tomography apparatus constructed in accordance with the principles of the present invention includes an evacuated chamber 1 in which an electron gun 2 having a heated cathode 3 is disposed. The electron gun 2 emits a focused electron beam 4. A focusing coil 6 is disposed at the end of the neck 5 of the evacuated chamber 1 for electron-optical focusing of the beam 4. A further coil 7 is also disposed at the end of the neck 5 of the chamber 1, the coil 7 functioning to deflect the beam 4. At the right side of FIG. 1, the chamber 1 is funnel-shaped. An annular anode 9 surrounding a measuring field 8 is disposed at an end face 10 of the chamber 1. The anode 9 has a surface 11 disposed at an angle other than 90° relative to the incident electron beam 4. The surface 11 is scanned or swept by the electron beam 4 in an orbital manner. The resulting x-ray beam 12 is gated in a known manner so as to be fan-shaped, with the plane of the fan being aligned with an opening 16 in the chamber 1 through which the x-ray beam 12 emerges. The fan plane proceeds perpendicularly to the plane of the drawing, and thus passes through a measuring field 8 from different directions so as to produce different projections of an examination subject 4 disposed on a support 13 as the electron beam 4 orbits the patient 14. A transverse slice of the patient 14 is thus penetrated by the x-ray beam 12 through various projections. The radiation profile of the x-ray beam 12 attenuated by the patient is acquired by an annular radiation detector 15. Corresponding electrical signals are supplied to a computer which calculates the attenuation values of a matrix of picture elements in the measuring field 8 therefrom. The attenuation values can be visually reproduced.

Figure 2:
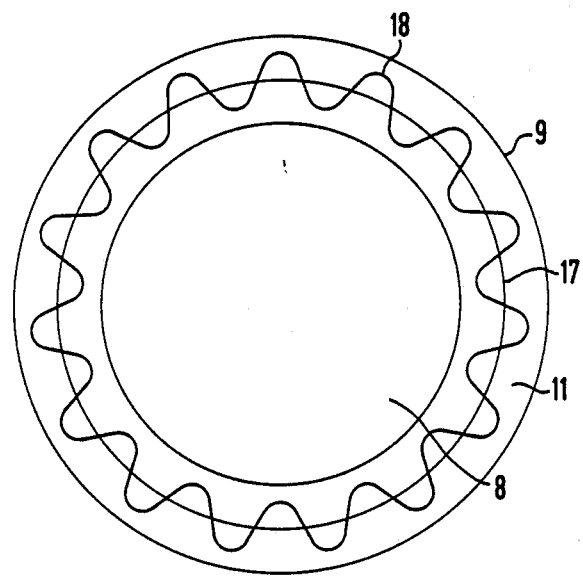
FIG. 2 is a plan view of the anode surface in the computer tomograph of FIG. 1 showing the focus path thereon.

The surface 11 of the anode 9, and the course of the focal spot thereon are shown in FIG. 2. An imaginary circle 17 is shown on the anode surface 11, the circle 17 being concentric with the anode 9. As can be seen, the focal spot path 18 periodically oscillates around the circle 17 in a wave-shaped path. This is achieved by suitable deflection of the electron beam 4 as described below.

It will be understood that the anode 9 need not surround the measuring field 8 in a closed ring, but may only partially surround the field 8, for example, semi-circularly.

The coil 7 is provided with a control unit 7a for controlling the sweep of the electron beam 4 in the radial direction, this sweep being overlayed on the movement of the electron beam 4 in the circumferential direction of the anode 9. A synchronization of the orbital, scanning sweep frequencies can be achieved with the control unit 7a. In particular, the sweep frequency can be selected such that one-fourth or one-half of the period of the sweep frequency, or a whole multiple thereof, is within the time between the registration of two samples belonging to one projection. In particular, the control unit 7a can operate such that the path of the focal spot crosses the circle 17 at the respective sampling times of the projections, or that the maxima or minima of the focal spot path 18 coincide with the sampling points in time.

Although modifications and changes may be suggested by those skilled in the art it is the intention of the inventors to embody within the patent warranted hereon all changes and modifications as reasonably and properly come within the scope of their contribution to the art.

I claim:

1. A computer tomography apparatus for generating an image of a slice of an examination subject comprising:

an anode having a continuous surface substantially surrounding said examination subject;
   means for generating an electron beam;
   means for deflecting said electron beam so as to be incident on said anode surface in an uninterrupted undulating wave path orbiting said examination subject to substantially the same extent as said anode surrounds said examination subject, so as to generate an x-ray beam directed at said examination subject from different directions; and
   control means connected to said means for deflecting for controlling orbital, sampling and sweep frequencies of said electron beam in synchronization so that one-fourth of the period of the sweep frequency, or a whole multiple of one fourth of the period, is less than the time between two samples for one projection of said examination subject.

2. A computer tomography apparatus as claimed in claim 1, wherein said control means is further defined as a control means connected to said means for deflecting for controlling the orbital, sampling and sweep frequencies of said electron beam in synchronization so that said wave-shaped path of said focus on said anode surface crosses an imaginary center circle on said surface coincident with the sampling points in time for a projection of said examination subject.

3. A computer tomography apparatus as claimed in claim 1, wherein said wave-shaped path has a plurality of periodic maxima, and wherein said control means is further defined as a control means connected to said means for deflecting for controlling the orbital, sampling and sweep frequencies of said electron beam in synchronization so that said maxima are coincident with the sampling points in time for a projection of said examination subject.

4. A computer tomography apparatus as claimed in claim 1, wherein said wave-shaped path has a plurality of periodic minima, and wherein said control means is further defined as a control means connected to said means for deflecting for controlling the orbital, sampling and sweep frequencies of said electron beam in synchronization so that said minima are coincident with the sampling points in time for a projection of an examination subject.

5. A computer tomography apparatus for generating an image of a slice of an examination subject comprising:

an anode having a continuous surface substantially surrounding said examination subject;
   means for generating an electron beam;
   means for deflecting said electron beam so as to be incident on said anode surface in an uninterrupted undulating wave path orbiting said examination subject to substantially the same extent as said anode surrounds said examination subject, so as to generate an x-ray beam directed at said examination subject from different directions; and
   control means connected to said means for deflecting for controlling orbital, sampling and sweep frequencies of said electron beam in synchronization so that one-half of the period of the sweep frequency, or a whole multiple of one half of the period, is less than the time between two samples for one projection of said examination subject.

6. A computer tomography apparatus as claimed in claim 5, wherein said control means is further defined as a control means connected to said means for deflecting for controlling the orbital, sampling and sweep frequencies of said electron beam in synchronization so that said wave-shaped path of said focus on said anode surface crosses an imaginary center circle on said surface coincident with the sampling points in time for a projection of said examination subject.

7. A computer tomography apparatus as claimed in claim 5, wherein said wave-shaped path has a plurality of periodic maxima, and wherein said control means is further defined as a control means connected to said means for deflecting for controlling the orbital, sampling and sweep frequencies of said electron beam in synchronization so that said maxima are coincident with the sampling points in time for a projection of said examination subject.

8. A computer tomography apparatus as claimed in claim 5, wherein said wave-shaped path has a plurality of periodic minima, and wherein said control means is further defined as a control means connected to said means for deflecting for controlling the orbital, sampling and sweep frequencies of said electron beam in synchronization so that said minima are coincident with the sampling points in time for a projection of an examination subject.

* * * * *